United States Patent [19]

Chen et al.

[11] Patent Number: 5,693,345

[45] Date of Patent: Dec. 2, 1997

[54] DIAMOND ANVIL CELL ASSEMBLY

[75] Inventors: Ruijin Chen, Towson, Md.; Bernard A. Weinstein, Williamsville, N.Y.

[73] Assignee: The Research Foundation of State University of New York, Amherst, N.Y.

[21] Appl. No.: 734,505

[22] Filed: Oct. 21, 1996

Related U.S. Application Data

[60] Provisional application No. 60/007,232, Nov. 2, 1995.

[51] Int. Cl.$^6$ .................................................. B29C 43/32
[52] U.S. Cl. ........................ 425/77; 264/319; 425/450.1; 425/DIG. 26
[58] Field of Search ............................ 425/77, 78, 589, 425/595, 451, 451.2, 450.1, DIG. 26; 264/319

[56] References Cited

U.S. PATENT DOCUMENTS

| | | |
|---|---|---|
| 3,509,597 | 5/1970 | Kirk . |
| 3,947,541 | 3/1976 | Barnes . |
| 4,386,950 | 6/1983 | Bell et al. . |
| 4,740,147 | 4/1988 | Asari et al. ........................ 425/77 |
| 4,776,223 | 10/1988 | Moss . |
| 5,295,402 | 3/1994 | Bovenkerk ........................ 425/77 |

FOREIGN PATENT DOCUMENTS

| | | |
|---|---|---|
| 1030005 A | 7/1983 | U.S.S.R. . |

OTHER PUBLICATIONS

A. Jayaraman, "The Diamond-Anvil High Pressure Cell", Scientific American, Apr. 1984, pp. 56–62.

B. A. Weinstein, "Cryogenic-Pressure Studies of Semiconductor Luminescence", Mat. Res. Soc. Symp. Proc. vol. 22, 1984, pp. 341–344.

B. A. Weinstein, "Cryogenic-Pressure Luminescence Studies of Defect Structure in Amorphous and Crystalline Chalcogenide Semiconductors", Solid State Physics Under Pressure, 1985, pp. 285–290.

B. A. Weinstein, "Effect of High Pressure on Radioactive Recombination in Hydrogenated Amorphous Silicon", Physical Review B, 15 Jan. 1981, pp. 787–793, vol. 23, No.2.

Advertisement, "Food-Lab" High Pressure Food Processors, date prior to 1995.

Specification Sheet, "Top Industrie-Annular Membrane Diamond Anvils Cell MDAC", date prior to 1995.

*Primary Examiner*—Jay H. Woo
*Assistant Examiner*—Joseph Leyson
*Attorney, Agent, or Firm*—John C. Thompson

[57] ABSTRACT

A diamond anvil cell assembly of relatively small diameter, so it may be used in commonly available cryostats, which cell assembly is capable of applying pressures in excess of 100 kbar. The pressure applying device of the diamond anvil cell assembly includes multiple bellows which are stacked apparently in series (i.e., end-to-end) but mechanically in parallel so that the force from each bellows adds without increasing the diameter of the assembly, thus multiplying the force of a single bellows ram by a factor of two or even four without increasing the diameter of the ram.

4 Claims, 3 Drawing Sheets

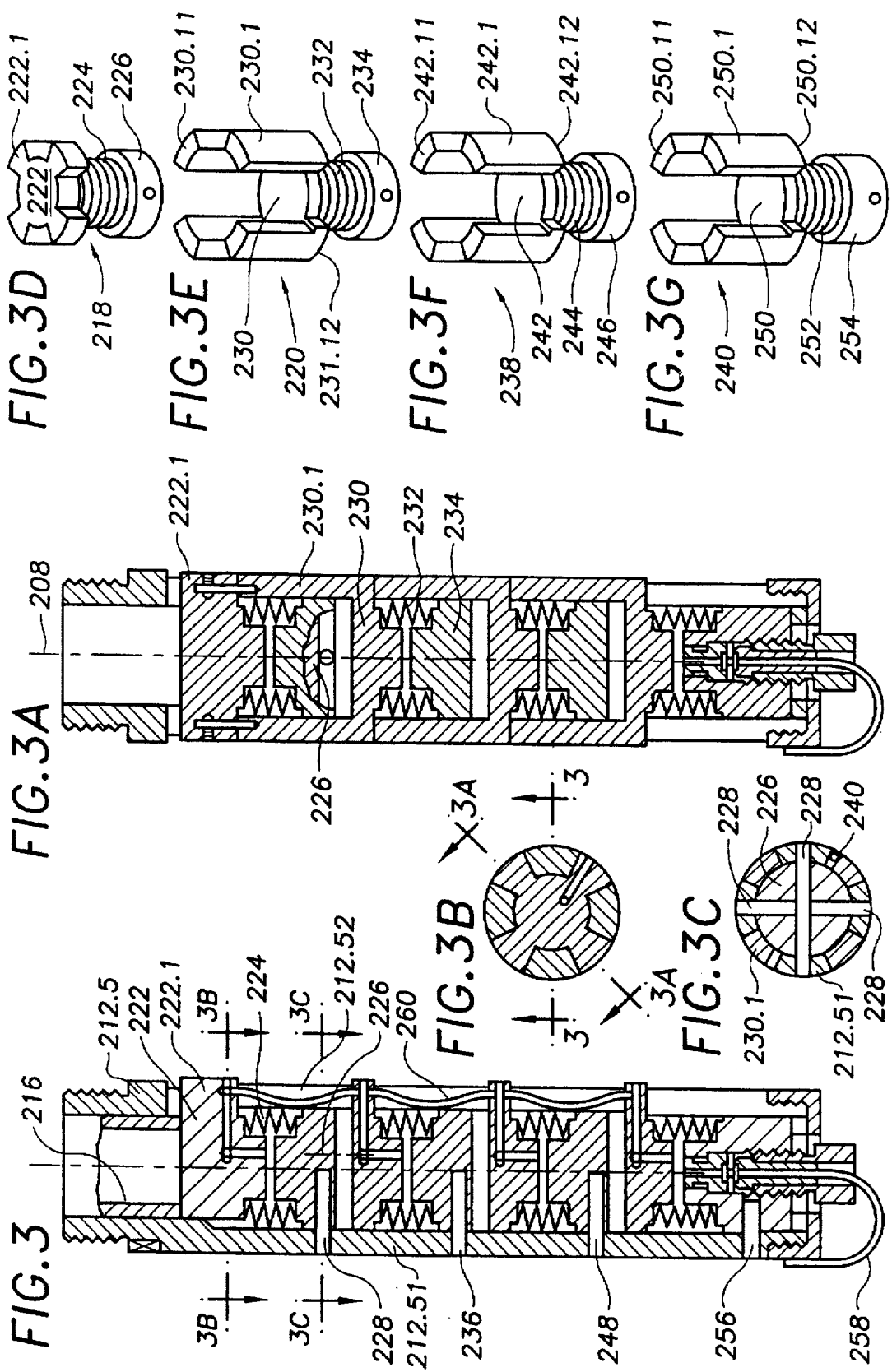

DIAMOND ANVIL CELL ASSEMBLY

This invention was made with Government support under Grant N00014-89-J-1797 awarded by the Department of the Navy. The Government has certain rights in the invention. This application claims the benefit under 35 U.S.C. § 119(e) of provisional application Ser. No. 60/007,232 filed Nov. 2, 1995 having the same title as this application.

TECHNICAL FIELD

The present invention relates generally to diamond anvil cell assemblies, and more particularly to a diamond anvil cell assembly of relatively small diameter, so that it may be used in commonly available cryostats, which cell assembly is capable of applying pressures in excess of 100 kbar, the pressure applying means of the diamond anvil cell assembly including multiple bellows which are stacked in such a way that their forces add without increasing the diameter of the assembly.

BACKGROUND OF THE INVENTION

As used in this description, a diamond anvil cell includes two faceted diamonds and their mounting structure, while the term diamond anvil cell assembly also includes the force applying means.

Diamond anvil cell assemblies (hereafter DACs) are used to create extremely high-pressure environments in which experiments may be conducted. A mechanically operated diamond anvil cell is illustrated in the April 1984 issue of the "Scientific American" at pages 54 through 62 and in U.S. Pat. No. 3,509,597. These DACs are more or less in the form of mechanically operated opposed-anvil presses, each of which includes two high quality brilliant-cut diamonds. The culet, which is the small flat face at the bottom (or point) of each of the diamonds, is enlarged to form a flat surface anvil normal to the optical axis of diamond. The anvil surfaces, when used in the applications contemplated by this invention, typically have a diameter of approximately 0.75 mm. One of the diamonds is held relatively stationary, and the other diamond is mounted for movement towards and away from the stationary diamond, the anvil surfaces of the diamonds facing each other. An apertured gasket, typically formed of metal, is sandwiched between the two diamonds. The small aperture in the gasket between the diamond anvil surfaces serves as the sample chamber, and, in operation, it contains the sample material to be studied and a fluid medium for applying hydrostatic pressure around the sample material. Force is applied to the movable diamond along the optical axis, so that the diamonds are squeezed together against the gasket, sealing the sample chamber. The sample is suspended in the medium and does not feel the direct diamond force. The gasket material flows under load, decreasing the diameter of the sample chamber, and thereby producing the tremendous increase in pressure.

It is of great interest to extend the DAC technique in a convenient way to high magnetic field far-infrared (FIR) spectroscopy. Such studies generally require cryogenic temperature because of the small energies of the FIR excitations. Furthermore, it is desirable that the pressure applied to the sample be changed in situ while the sample stays motionless in the magnetic field and FIR beam. Previous cryogenic FIR work with DACs has employed clamp-type DACs which do not permit in situ pressure tuning. This has been a major drawback since it hampers the ability to calibrate pressure and reproduce results, makes it difficult to observe resonances and anti-crossings between energy levels, and precludes studying many phenomena that exhibit thermal metastability.

The principal difficulties in adapting prior pressure tunable DAC designs to FIR magneto-spectroscopy arise from the space constraints usually present inside a magnet-cryostat bore. The existing tunable DAC options fall into three groups. In the first group, the full force is generated outside the cryostat (by mechanical or hydraulic means) and then transmitted to the diamond anvil cell through linkages, typically a pair of coaxial tubes, one in tension and the other in compression. Bowden cables also have been used as the linkages to reduce the size and heat load. In the second group, a small force or torque is transmitted down the cryostat and then amplified using levers or screws close to the diamond anvil cell. Both of these methods present difficulties for FIR magneto-spectroscopy since the force-transmitting tubes, cables, or linkages must, of necessity, extend into the region of high magnetic field and low temperature. Hence, they often block FIR access to the diamond anvils, introduce substantial heat losses, and may disturb the field unless non-magnetic materials (with the drawback of lower strength) are used.

In the third design group, the driving force is generated by pressurizing a bellows (or diaphragm) chamber that is incorporated into the DAC. These designs allow the force to be generated at cryogenic temperatures by a ram making it much easier to maintain FIR access without disturbing the field. Practically, the best medium to pressurize the bellows is He with a freezing pressure of 13.8 MPa (2000 psi) at 4.2° K. This leads to a major limitation of the force available using existing single bellows designs in small bore cryostats at low temperatures, the force available being equal to the He pressure times the effective area of the bellows. Assuming reasonable diamond anvil tip sizes (0.4–0.8 mm), for FIR spectroscopy, a force of up to 10 kN is required to achieve diamond anvil cell pressures above 30 GPa. However, in order to generate 10 kN at a temperature down to 4.2° K, the bellows outer diameter must be at least 1.5 in. (the effective diameter is the average of the inner and outer diameters). Allowing for the harness holding the bellows and possibly a vacuum can enclosing the DAC, this generally would require a cryostat bore exceeding 2.0 inches. Most superconducting magnets have a relatively small bore less than 1.50 inches in diameter. In the past the only practical way of achieving high DAC pressure at cryogenic temperature through the use of liquid helium-operated bellows was to increase the diameter of the bellows to achieve a greater force. However, superconducting magnet cryostats which are capable of accepting such large diameter assemblies are extremely (and usually prohibitively) expensive.

OBJECTS AND SUMMARY OF THE INVENTION

It is an object of the present invention to provide a fluid-pressure operated diamond anvil cell assembly capable of applying high pressures exceeding 150 kbar in the sample chamber at cryogenic temperatures and in high magnetic fields wherein the diamond anvil cell assembly does not exceed bore diameter of commonly available cryostats, and wherein the force applied to the diamond anvil cell can be varied in situ.

More particularly, it is an object of the present invention to provide a diamond anvil cell which is suitable for use at cryogenic temperatures and in high magnetic fields, the diamond anvil cell being driven by a liquid helium-pressurized ram, the force of the ram being generated by two or more bellows which are stacked in such a way that the forces add without increasing the diameter of the ram.

In summary, the size limitation of conventional DAC's operated by bellows rams is overcome by stacking several bellows apparently in series (i.e., end-to-end) but mechanically in parallel so that the force from each bellows adds. The principal advantage of operating the DAC ram by multiple additive bellows over the previous single bellows ram operator is that it multiplies the force of a single bellows ram by a factor of 2 or even 4 without increasing the diameter of the ram.

The foregoing objects are achieved by providing a tubular frame assembly which carries a first diamond anvil at the bottom of a cylindrical bore. The tubular frame assembly also carries a ram assembly mounted within the bore, the ram assembly having a second diamond anvil which can be forced toward the first diamond anvil. In accordance with this invention the tubular frame assembly is provided with a plurality of elongated fingers which define elongated slots parallel to the axis of the tubular bore. A first bellows assembly is provided which has a first top plate which bears against the ram and a first bellows subassembly interconnected with the elongated fingers and capable of forcing the top plate against the ram assembly when liquid helium is introduced into the bellows subassembly. This invention is further characterized by a second bellows assembly stacked upon the first bellows assembly, the second bellows assembly having a second top plate and a second bellows subassembly. The top plate has elongated arms received within the elongated slots of the tubular frame assembly, the ends of the arms bearing against the first top plate of the first bellows. The second bellows subassembly is interconnected with the elongated fingers so that when liquid helium is introduced into the second bellows subassembly an additive force will be applied to the first top plate of the first bellows assemblies.

The foregoing objects and advantages of this invention will become more apparent after a consideration of the following detailed description taken in conjunction with the accompanying drawings in which preferred forms of this invention are illustrated.

BRIEF DESCRIPTION OF THE DRAWINGS

FIG. 3 is a sectional view taken generally along the line 3—3 in FIG. 3B showing a four-stage diamond anvil cell assembly employing four bellows.

FIG. 3A is a view similar to FIG. 3, this view being taken generally along the line 3A—3A in FIG. 3B.

FIG. 3B is a section taken generally along the line 3B—3B in FIG. 3.

FIG. 3C is a section taken generally along the line 3C—3C in FIG. 3.

FIGS. 3D through 3G are perspective views of portions of the four-stage diamond anvil cell shown in FIGS. 3 and 3A.

DETAILED DESCRIPTION

Figure 1A:
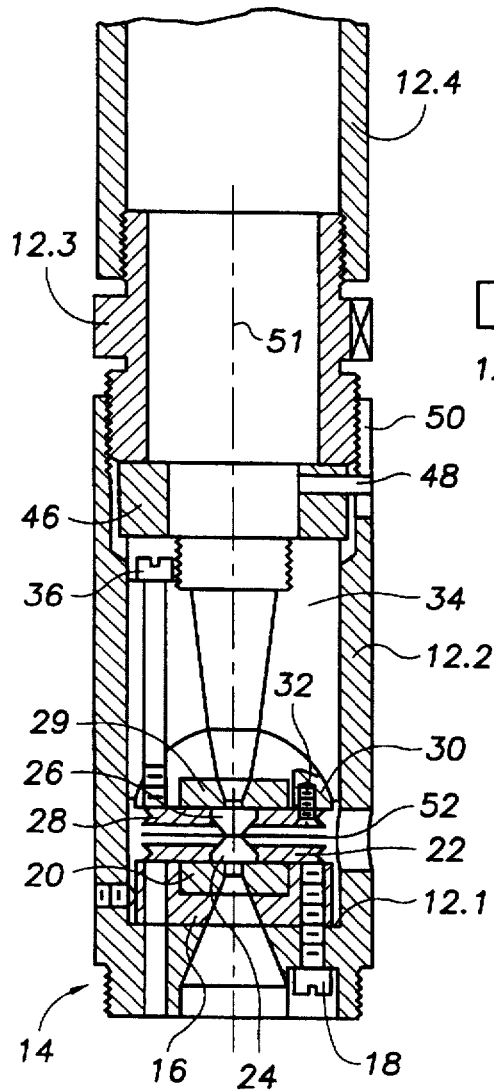
FIG. 1A is an enlarged section view of a prior art design of a diamond anvil cell.
Figure 1:
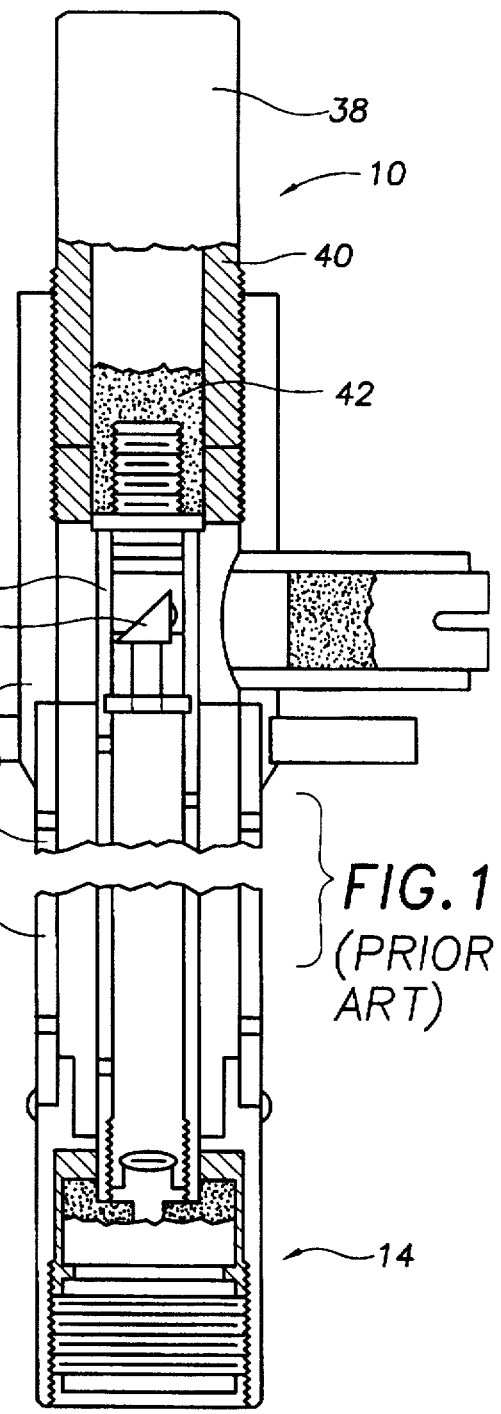
FIG. 1 is a sectional view through a prior art design of a diamond anvil cell assembly.

Diamond anvil cell assemblies for use in cryostats are well known in the prior art, and one such assembly is shown in FIG. 1, this view corresponding to the diamond anvil cell illustrated on page 286 of *SOLID STATE PHYSICS UNDER PRESSURE: Recent Advance with Anvil Devices* published by D. Reidel Publishing Company in 1985. A more recently developed prior art diamond anvil cell is shown in FIG. 1A. In the illustrated prior art designs, the diamond anvil cell assembly is indicated generally at 10 and includes a tubular ram frame assembly 12 which includes a cell body 12.2 (FIG. 1A), a cell clamp nut 12.3 and a tension tube 12.4. Mounted within the cell body 12.2 is a diamond anvil cell indicated generally at 14. To this end the cell body 12.2 is provided with a shoulder 12.1 upon which a mounting plate 16 is secured in place by two screws 18, only one of which is shown in FIG. 1A. A backing plate 20 is received in a circular recess (no number) on the mounting plate 16, the upper surface of the backing plate being flush with the upper surface of the mounting plate. A retaining ring 22 is positioned on the upper surface of the backing plate and mounting plate and captures a brilliant-cut gem-quality diamond 24 which has had its culet enlarged to serve as an anvil as is well known in the art. As can be seen from FIG. 1A the mounting plate 16, backing plate 20, and cell body 12.2 are all provided with suitable apertures to permit optical access to the diamond 24 from below as shown in FIG. 1A.

A second diamond anvil 26 is formed in the same way as the first diamond anvil 24. The second diamond anvil is mounted within a retaining ring 28 which is secured to a rocker 30 by three screws 32, only one of which is shown. The rocker 30 is in turn secured to a piston 34 by three screws 36, only one of which is shown. The purpose of the rocker 30 is to permit the anvil surface (or culet) of the second diamond 26 to be positioned precisely parallel to the anvil surface (or culet) of the first diamond 24. Thus, the rocker 30 can be secured in such a position so that this can be achieved. The piston 34 is slidable within the cylindrical bore of the cell body 12.2 and is forced downwardly by means of a hydraulic cylinder assembly 38. The cylinder assembly includes a cylinder 40 which is screwed into the upper end of the tubular frame assembly 12, and a piston 42 movable within the cylinder 40. Means for applying a hydraulic force to the piston is provided (not shown) and when the piston is moved downwardly it will, acting through a piston rod extension 44 and a non-rotatable ring 46, bear down against the piston 34 to force the second diamond anvil 26 towards the first diamond anvil 24. To hold the ring 46 from rotation, one end of a pin 48 is received within the ring 46, and the other end of the pin 48 is received within a slot 50 in the cell body 12.2. The purpose of the ring 46, pin 48 and slot 50 is to ensure that the diamonds do not rotate with respect to one another as a compressive force is applied along the axis 51 or centerline of the assembly.

In operation, as explained above, the anvils will not actually come in contact with each other but will be separated from one another by an apertured metal gasket 52, which aperture contains the sample in a hydrostatic fluid medium. As can be seen from FIG. 1, the piston rod extension 44 is hollow and this permits additional optical access through prism 54. Unfortunately, the prior art designs which are typically illustrated in FIGS. 1 and 1A do not permit the use of FIR infrared spectroscopy in high magnetic-field cryogenic environments because the piston rod extension 44 blocks FIR access to the diamond anvils. Also, the piston rod extension will transmit heat from the cylinder assembly 38 (at room temperature) to the sample, making it difficult to maintain the sample at the desired cryogenic temperature.

In order to overcome the problems associated with the piston rod extension 44, it has been proposed in the past to mount a piston assembly entirely within a superconducting magnet. However, this proposal has not proven to be satisfactory because the approximate relationship between the pressure P achieved within the hole in the gasket 52 (i.e., sample chamber of the diamond anvil cell, and the applied driving force F is $$P = 4/d^2(F - F_o) \quad (1)$$

Here d is the diameter of the diamond anvil (or culet) surface, and $F_o$ is the minimum force needed to produce plastic flow in the gasket metal when squeezed between the diamonds. With typical 0.75 mm (0.03 in) culets, an excess force $F-F_o=500$ lb gives a pressure of about 2,000,000 lbs/in$^2$ or 150 kbar (viz., 150,000 times atmospheric pressure). However, no pressure is obtained if F does not exceed $F_o$, which limit is typically 350–600 lb to produce plastic flow in most hardened steels. Hence, a single ram (constrained by the same cryostat bore) would not be able to pressurize the sample chamber of the diamond anvil cell at 4.2° K because the maximum ram force could not exceed the threshold force $F_o$. In accordance with this invention a multiple ram is used to pressurize the sample chamber in a force additive design to overcome the limitations of small bore magnet-cryostats, thus allowing the driving force F to far exceed $F_o$ at cryogenic temperatures.

Figure 2A:
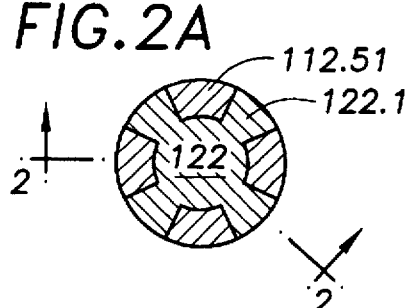
FIG. 2A is sectional view taken generally along the line 2A—2A in FIG. 2.
Figure 2B:
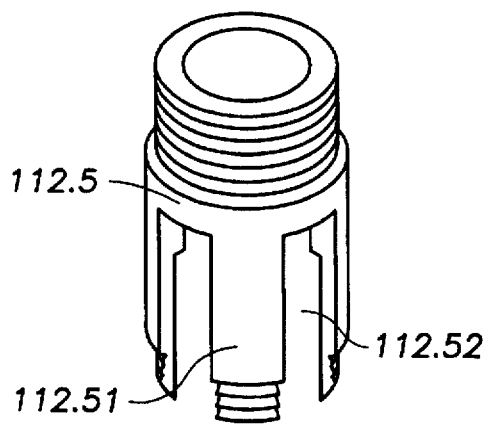
FIGS. 2B, 2C, and 2D are perspective views of portions of the diamond anvil cell assembly shown in FIG. 2.
Figure 2C:
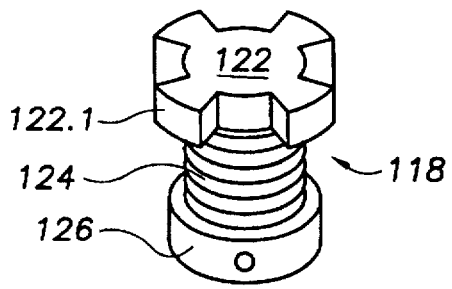
Figure 2D:
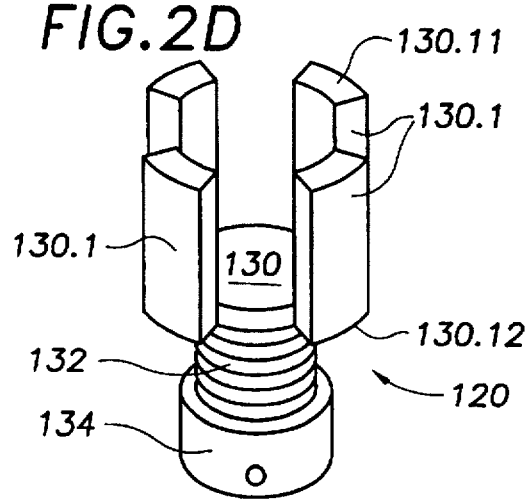
Figure 2:
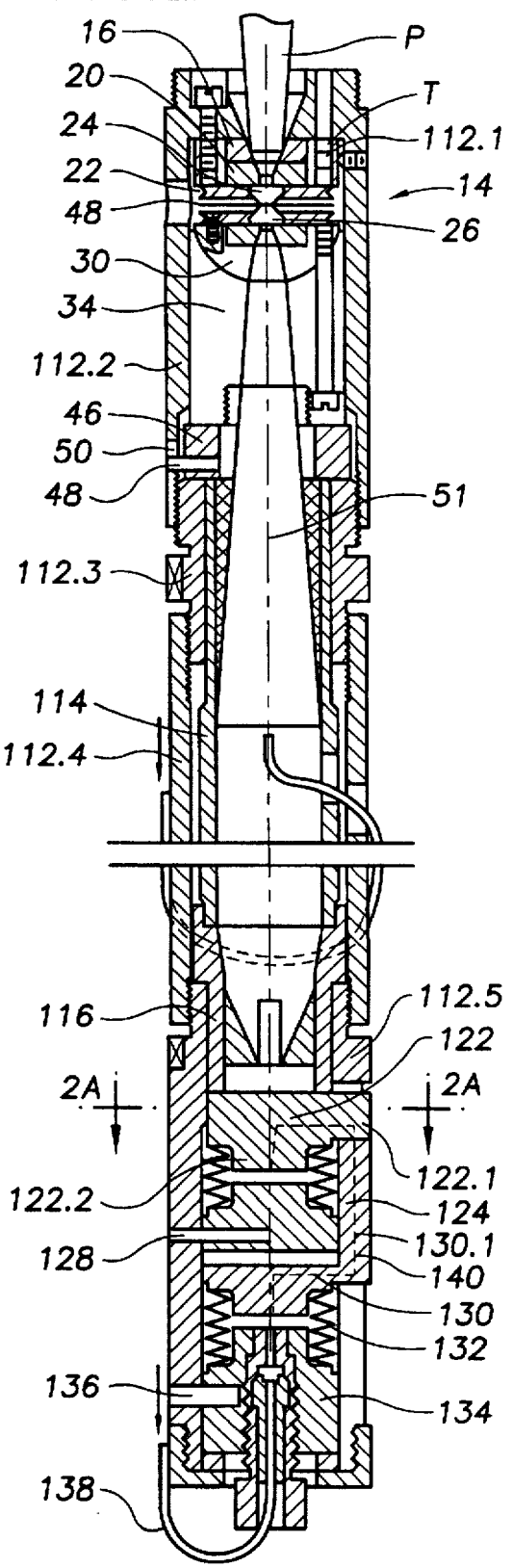
FIG. 2 is a sectional view through a diamond anvil cell assembly employing a pair of stacked force applying means, this view being taken generally along the line 2—2 in FIG. 2A.

With reference now to FIGS. 2 through 2D, a two-stage multi-bellows ram is illustrated engaged with a diamond anvil cell which overcomes the disadvantages of the prior art. As in the prior art design, the diamond anvil cell, (which is shown at the top in FIG. 2 rather than at the bottom as in FIG. 1) includes first and second diamond anvils 24, 26, the first diamond anvil 24 being mounted in a retaining ring 22 supported upon backing plate 20 and mounting plate 16, and the second diamond anvil 26 being mounted in the same manner as is shown in FIG. 1A. In addition, a temperature sensor T and input far-infrared light focusing paraboloidal cone P are also illustrated. The ring 46 is kept from rotating by a pin 48 received within a slot 50 in the cell body 12.2 of the tubular ram frame assembly 12. As can be seen from an inspection of FIG. 2, the tubular ram frame assembly is formed of a number of components which include a cylindrical cell body 112.2 (which is provided with a shoulder 112.1 against which the mounting plate 16 abuts), a cell clamp nut 112.3, a tension tube 112.4, and a ram frame 112.5. As can be seen from FIG. 2B, the ram frame 112.5 is provided with a plurality of elongated fingers 112.51 which define elongated slots 112.52 parallel to the axis 51 of the cylindrical bore. Forces are applied to the diamond anvil cell by the novel multiple-stacked hydraulic force applying means of this invention. The force applying means each being carried by the ram frame 112.5 and being connected to the ram assembly (including adapter 116, compression tube 114, anti-rotation ring 46, piston 34, rocker 30, backing plate 29) in such a manner that the forces of the force supplying means add without increasing the diameter of the diamond anvil cell assembly. To this end, the multiple-stacked hydraulic force applying means of this embodiment includes first and second bellows assemblies indicated generally at 118, and 120, respectively. The first bellows assembly 118 includes a first top plate 122 having radially outwardly extending projecting portions 122.1 which are slidably received within the slots 112.52. The first top plate is moved by a first bellows subassembly including a first bellows 124 and a first bottom plate 126. As can be seen from FIG. 2 the first top plate also has a downwardly extending centrally located cylindrical boss about which one end of the first bellows 124 is disposed. The other end of the first bellows 124 bears against the first bottom plate 126 which is disposed entirely within the fingers 112.51 and is secured thereto by four pins 128, only one of which is shown. It can be appreciated that if the hydraulic fluid under pressure, such as liquid helium at 4.2° K is introduced into the bellows chamber that, since the first bottom plate is secured to the tubular ram frame assembly 112.51, the first top plate 122 will move upward forcing the ram assembly to move the second diamond anvil 26 towards the first diamond anvil 24.

In accordance with this invention, a second bellows assembly 120 is stacked upon the first bellows assembly 118 in such a manner that the diameter of the two bellows assemblies will not exceed the diameter of a single bellows assembly, but also in such a manner that the force of the second bellows assembly will be additive to the force of the first bellows assembly. To this end, the second bellows assembly includes a second top plate 130 having elongated arms 130.1 (FIG. 2D) received within the elongated slots 112.52, each of the arms of the second top plate 130 having a first and second ends 130.11 and 130.12, respectively, the first end 130.11 of the arms 130.1 bearing against the radially outwardly extending extensions 122.1 of the first top plate of the first bellows assembly. The second bellows assembly also has a second bellows subassembly which includes a second bellows 132 and a second bottom plate 134 which is pinned or otherwise rigidly secured to the fingers 112.51 via four pins 136. It can be appreciated that if hydraulic fluid is introduced into the second bellows 132 that the top plate 130 will be moved upwardly causing it to bear against the first plate 122 which will in turn bear against the ram assembly. Hydraulic fluid is introduced into the second bellows 132 by means of a capillary tube 138. The hydraulic chamber within the bellows 132 is in turn connected to the hydraulic chamber within the bellows 124 by means of further capillaries indicated by the broken line 140.

A double bellows prototype version of such a ram has been constructed, along with a mating diamond anvil cell for use in a 1.42 in. (36 mm) bore superconducting magnet. The overall ram diameter is only 26 mm. Each bellows has an effective area of 16.5 mm$^2$, and a burst pressure of 27.6 MPa. Thus, the two-stage ram is capable of generating a maximum force of 5 kN when pressurized to 13.8 MPa, the freezing pressure of He at 4.2° K. With this maximum force of 5 kN, this ram has so far brought the sample chamber of the diamond anvil cell up to a pressure of 19.5 GPa using 0.75 mm anvil tips. With this apparatus, the pressure, magnetic field and temperatures can each be tuned in situ over the ranges of 0–20 GPa, 0–15 T and 2°–300° K without removing the DAC probe from the magnet cryostat. A force of 10 kN could be easily generated by scaling the design up to a four-stage bellows ram. Such a four-stage bellows ram has been designed and its overall diameter remains 26 mm.

While a double bellows design has been illustrated in FIGS. 2 through 2D, other designs may be used for adding forces to a ram in a diamond anvil cell without increasing the diameter of the diamond anvil cell. FIGS. 3–3G show a four bellows design. In these figures the diamond anvil cell has not been illustrated. In these figures the same reference numerals will be applied as applied in FIGS. 2 through 2D except that they will begin with 2 instead of 1. Thus, there is a ram frame 212.5 having longitudinally extending fingers 212.51 which define slots 212.52 which are parallel to the axis 208 of the ram frame assembly. Mounted within the bore of the ram frame 212.5 is an adapter 216. The first bellows assembly 218 includes a first top plate 222 which bears against the lower end of the adapter 216, the top plate being forced upwardly by hydraulic fluid within the first bellows subassembly which includes a bellows 224 which extends between the movable first top plate 222 and the first bottom plate 226 which is secured to the fingers 212.51 by four equally spaced apart pins 228 as can best be seen from FIG. 3C. The second bellows assembly 220 includes a second top plate 230 having elongated arms 230.1 received within the elongated slots 212.52, each of the elongated arms having first and second ends 230.11 and 230.12, respectively, the first ends 230.11 bearing against the bottom surface of the radial extensions 222.1 of the first top plate. In addition, the second bellows assembly also includes a second bellows subassembly having a second bellows 232 and a second bottom plate 234, the second bottom plate being secured to the fingers 212.51 by pins 236. In this design, third and fourth bellows assemblies 238 and 240 are additionally provided. Each of these bellows assemblies are essentially identical to the second bellows assembly. Thus, the third bellows assembly includes a third top plate 242 having elongated arms 242.1 received within the slots 212.52, each of the arms having a first end 242.11 and a second end 242.12, the first end 242.11 bearing against the second end 230.12 of the elongated arms of the second top plate 230. The third bellows assembly also includes a third bellows bellows subassembly having a third bellows 244 and a third bottom plate 246. The third bottom plate is also secured to the fingers 212.51 by pins 248. Finally, the fourth bellows assembly includes a fourth top plate 250 having elongated arms 250.1 each of the arms having first and second ends, 250.11 and 250.12, respectively. The fourth bellows assembly also includes a fourth bellows subassembly including a bellows 252 and a bottom plate 254. The fourth bellows is mounted below the fourth top plate and when it receives hydraulic fluid, such as liquid helium under pressure, it will force the top plate upwardly pushing the first ends 250.11 of the elongated arms against the second end of the elongated arms 242 of the third top plate. Mounted below the bellows 252 is a fourth bottom plate which is secured to the fingers 212.51 by pins 256. Hydraulic fluid is introduced into the lowermost bellows by means of a capillary tube 258, the lowermost bellows being interconnected via additional capillary tubes 260 to the other bellows. With this construction it can be seen that, as hydraulic fluid is introduced into the system, the forces of the various bellows assemblies are additive, thus creating a much greater force upon the adapter 216 than is possible with a single bellows.

While preferred forms of this invention have been described above and shown in the accompanying drawings, it should be understood that applicant does not intend to be limited to the particular details described above and illustrated in the accompanying drawings, but intends to be limited only to the scope of the invention as defined by the following claims.

What is claimed is:

1. A diamond anvil cell assembly of relatively small diameter; the diamond anvil cell including:

a tubular ram frame assembly having an elongated cylindrical bore;

a first diamond anvil mounted at one end of the bore in the tubular ram frame assembly;

a ram assembly slidably mounted within the cylindrical bore for movement towards and away from the first diamond anvil;

a second diamond anvil carried by an end of the ram assembly; and the improvement comprising multiple stacked hydraulic force applying means each carried by the tubular ram frame assembly and each being connected to the ram assembly in such a manner that the forces of the force applying means add without increasing the diameter of the diamond anvil cell assembly.

2. A diamond anvil cell assembly of relatively small diameter capable of applying high pressures exceeding 100 kbar at cryogenic temperatures, the diameter not exceeding the bore diameter of commonly available cryostats and the diamond anvil cell being operated by fluid pressure; said diamond anvil cell comprising:

a tubular ram frame assembly having an elongated cylindrical bore, a portion of the tubular ram frame assembly being provided with a plurality of elongated fingers which define elongated slots parallel to the axis of the cylindrical bore, a first diamond anvil mounted at one end of the bore in the tubular ram frame;

a ram assembly slidably mounted within the cylindrical bore for movement towards and away from the first diamond anvil;

a second diamond anvil carried by an end of the ram assembly;

a first bellows assembly including a first top plate which bears against one end the ram assembly, and a first bellows subassembly for forcing the first top plate against one end of the ram assembly when liquid helium is introduced into the first bellows subassembly; and a second bellows assembly including a second top plate having elongated arms received within the elongated slots of the tubular ram frame assembly, each of the arms of the second top plate having first and second ends, the first ends of the arms bearing against the first top plate of the first bellows assembly, and a second bellows subassembly for applying force to the second top plate for causing the first ends of the arms on the second top plate to apply an additive force to the first top plate of the first bellows assembly.

3. A diamond anvil cell assembly as set forth in claim 2 wherein a third bellows assembly is provided, the third bellows assembly including:

a third top plate having elongated arms received within the elongated slots of the tubular ram frame assembly, each of the arms of the third bellows assembly having first and second ends, the first ends of the arms of the third bellows assembly bearing against the second ends of the arms of the second bellows assembly, and a third bellows subassembly for applying force to the third top plate for causing the first ends of the arms on the third top plate to apply an additive force to the arms of the second top plate to apply an additive force to the first top plate of the first bellows assembly.

4. A diamond anvil cell assembly as set forth in claim 3, further including:

a fourth bellows assembly including
a fourth top plate having elongated arms received within the elongated slots of the tubular ram frame assembly, each of the arms of the fourth top plate having first and second ends, the first ends of the arms of the fourth top plate bearing against the seconds ends of the arms of the third top plate, and
a fourth bellows subassembly for applying force to the fourth top plate for causing the first ends of the arms of the fourth top plate to apply an additive force to the first top plate of the first bellows assembly.

* * * * *